United States Patent [19]
Kenny et al.

[11] Patent Number: 5,455,032
[45] Date of Patent: Oct. 3, 1995

[54] USE OF PHOSPHOCHOLINE HAPTEN CONJUGATES IN VACCINES

[75] Inventors: James J. Kenny, Rockville; Dan L. Long, Kensington, both of Md.

[73] Assignee: The United States of America as represented by the Department of Health and Human Services, Washington, D.C.

[21] Appl. No.: 99,205

[22] Filed: Jul. 29, 1993

[51] Int. Cl.$^6$ .................. A61K 39/385; A61K 39/09; C07K 17/00

[52] U.S. Cl. .................. 424/194.1; 530/404; 530/405; 530/408; 530/409; 424/197.11; 424/244.1

[58] Field of Search .................. 530/404, 405, 530/408, 409; 424/194.1, 197.11, 244.1

[56] References Cited

U.S. PATENT DOCUMENTS 4,451,404  5/2984  Van Rheenen.

OTHER PUBLICATIONS

Laleral (1989) Clin. Exp. Immunol. 75:52–57.
Wallick et al. (1983) J. Immunol. 130(6):2871–2875.
Gupta et al. (1993) Vaccine 11(3):293–306.
Allison et al. in "Vaccines: New Approaches to Immunological Problems" ed. R. W. Ellis 1992 Butterworth–Heinemann, pp. 431–449.
Briles, David E. (1992) "Mouse Antibody to Phosphocholine Can Protect Mice from Infection with Mouse–Virulent Human Isolates of *Streptococcus pneumoniae*", *Infection and Immunity*, 60:1957–1962.
Brown, Mckay, et al. (1984) "Subpopulations of Antibodies to Phosphocholine in Human Serum", *the Journal of Immunology*, 132:1323–1328.
Bruderer, Urs, et al. (1989) "Antibody Combining Site Heterogeneity Within the Response to Phosphocholine Keyhole Limpet Hemocyanin", *Molecular Immunology* 26:63–71.
Kenny, James J., et al. (1991) "Receptor–Mediated Elimination of Phosphocholine–Specific B Cells in X–linked Immune–Deficient Mice", *The Journal of Immunology*, 146:2568–2577.
Mond, James J., et al. (1977) "Inability of Mice With a Defect in B–Lymphocyte Maturation to Respond to Phosphorylcholine on Immunogenic Carriers", *The Journal of Experimental Medicine*, 146:1138–1142.
Spande, Thomas F. (1980) "Synthesis of Two Novel Phosphorycholine Esters for Probes in Immunological Studies" *Journal of Organic Chemistry*, 45:3081–3084.
Wallick, Susan, et al. (1983) "Resistance to *Streptoccous pneumoniae* is Induced by a Phosphocholine–Protein Conjugate", *The Journal of Immunology*, 130:2871–2875.
Wicker, Linda S. (1982) "Antibodies from the Lyb–5⁻ B Cell Subset Predominate in the Secondary IgG Response to Phosphocholine", *the Journal of Immunology*, 129:950–953.
Wicker, Linda S., et al. (1983) "The Asymmetry in Idiotype–Isotype Expression in the Response to Phosphocholine is Due to Divergence in the Expressed Repertoires of Lyb–5$^+$ and Lyb–G$^-$ Cells", *the Journal of Immunology*, 131:2468–2476.
Yother, Janet, et al. (1982) "Protection of Mice from Infection with *Streptococcus pneumoniae* by Anti–Phosphocholine Antibody", *Infection and Immunity*, 36:184–188.

*Primary Examiner*—Kay K. A. Kim
*Attorney, Agent, or Firm*—Townsend and Townsend and Crew

[57] ABSTRACT

This invention relates to compositions useful for inducing immunoprotection against infections by pathogenic organisms containing phosphocholine antigens, including *Streptococcus pneumoniae* and other microorganisms that have a phosphocholine antigen component of their membranes or capsids. This invention also relates to vaccines and methods for inducing immunoprotection against infection by these pathogenic organisms.

19 Claims, 4 Drawing Sheets

USE OF PHOSPHOCHOLINE HAPTEN CONJUGATES IN VACCINES

BACKGROUND OF THE INVENTION

A. Field of the Invention

This invention relates to compositions useful for inducing immunoprotection against infections by pathogenic organisms containing phosphocholine antigens, including *Streptococcus pneumoniae* and other microorganisms that have a phosphocholine antigen component in their capsules or membranes. This invention also relates to vaccines and methods for inducing immunoprotection against infection by these pathogenic organisms.

B. Background

Phosphocholine is an antigenic component in a variety of pathogenic organisms. These include a variety of bacteria which contain phosphocholine as a component of the bacterial cell wall. Examples of such bacteria include Streptococcus group O +H bacteria, *Streptococcus pneumoniae*, various species of Pseudomonas and *Proteus Morganii*, and *Lactobacillus acidophilus*. Fungi include Trichoderma, Fusarium and Aspergillus. In addition, there are a variety of parasites, including parasitic nematode worms such as Ascaris and Nippostrongeloides which have phosphocholine antigens.

*Streptococcus pneumoniae* remains an important pathogenic bacterium even with anti-microbial therapies available for its treatment. It is a commensal, normally non-pathogenic bacterium found in many individuals from infancy through adulthood, but as an opportunistic pathogen is responsible for several diseases. Three of these diseases, bacteremia, pneumonia and meningitis, are life threatening unless there is active intervention. Currently, the treatment most often prescribed involves the use of penicillin analogues or erythromycin, but recently an increasingly higher incidence of penicillin and multi-drug resistant strains have been isolated.

It is preferable to vaccinate against *S. pneumoniae* rather than treat the disease, both to reduce the incidence of pneumococcal diseases and to overcome the problem of the antibiotic resistant strains. An effective vaccine against *S. pneumoniae* should be given early in life, because infants may routinely suffer multiple episodes of *S. pneumoniae* infections by two years of age. Additionally, an ideal vaccine needs to be cross-reactive between all the various strains of *S. pneumoniae*. This is particularly relevant for *S. pneumoniae* since the pathogenic strains vary geographically.

The current pneumococcal vaccine is composed of the purified capsular polysaccharides from 23 of the 83 different strains of *S. pneumoniae*, including the strains most prevalent in specific pathological conditions in the United States. In normal adults, the current pneumococcal polysaccharide vaccine is 80% effective at preventing infection with *S. pneumoniae*, but it is much less effective in infants, and in senescent and immunocompromised patients. Unfortunately these groups represent some of the high risk populations most in need of the protection.

A type specific antibody response is achieved in non-infant recipients for most of the *S. pneumoniae* strains represented in the vaccine. However, some of the more important pathogenic strains do not induce antibody responses in children under five years of age. Repeat immunizations do not significantly improve this situation in children under the age of two years. There are also clear instances where vaccination has failed to produce protective antibodies to the homologous strain in this age group. This is primarily because infants lack the immunological maturity to produce anti-carbohydrate antibodies.

There is the additional problem that the vaccine is less effective in geographic areas where the common pathogenic strains are not included in the vaccine. Construction of the vaccine was based on the epidemiological studies of Europe and the United States, so this affects geographic areas primarily outside the United States and Europe. The failure of the current pneumococcal capsular vaccine to protect those individuals most at risk for infection with *S. pneumoniae* and the geographical limitations of the current vaccine indicate that a more comprehensive streptococcal vaccine capable of overcoming these problems is needed.

This invention relates to phosphocholine conjugates capable of protecting normal or immunocompromised animals, including humans, from infection from pathogenic organisms. Examples of such pathogenic organisms include *S. pneumoniae* and other bacteria having a phosphocholine (PC) component in their cell walls. These conjugates are haptens containing phosphocholine which are conjugated to carrier molecules or substances. The invention also relates to vaccines based on these phosphocholine conjugates and to methods of immunizing animals, including humans, to infection by *S. pneumoniae* and other pathogenic organisms having PC as a component of their cell membranes or capsids.

SUMMARY OF THE INVENTION

The invention provides for PC conjugates which are capable of eliciting an immune response in animals. These PC conjugates have a straight chain alkyl group linking the PC moiety to a variety of immunological carriers via an amide linkage. The invention also provides for vaccines containing these PC conjugates which are capable of inducing immunoprotection in animals against a variety of pathogenic organisms containing PC antigens.

The invention also provides for methods of protecting animals from infection by PC antigen-containing pathogenic organisms. These methods involve administration of vaccines containing the PC conjugates of the invention.

BRIEF DESCRIPTION OF THE DRAWINGS

Mice were immunized twice with 200 µg of EPC-KLH as described in Example 1, herein. Seven days following the 2° immunization (day 21), mice were challenged with virulent *S. pneumoniae* (strain WU-2) at various doses. Open squares represent unimmunized controls challenged with 10 bacteria and inverted closed triangles represent EPC-KLH immune C.CBA/N mice challenged with $10^4$ bacteria.

Mice were immunized with DPPC:KLH as described in example 3 herein and then challenged i.p. with $10^3$ (open symbols) or $10^4$ (closed symbols) of *S. pneumoniae* type 3, strain WU-2. Data represent survival curves of 5 to 10 mice per group.

Mice were immunized with DPPC:KLH as described in example 3 herein and then challenged i.p. with $10^3$ (open symbols) or $10^4$ (closed symbols) of S. pneumoniae type 3, strain WU-2. Data represent survival curves of 5 to 10 mice per group.

Mice were immunized EPC:KLH as described in Freund's Adjuvant as described in example 3 herein and were then challenged i.p. $10^4$ (closed symbols) of S. pneumoniae type 3, strain WU-2. Data represent survival curves of 5 to 10 mice per group. Unimmunized controls (squares) were challenged with 100 bacteria.

Mice were immunized EPC:KLH as described in Freund's Adjuvant as described in example 3 herein and were then challenged i.p. $10^4$ (closed symbols) of S. pneumoniae type 3, strain WU-2. Data represent survival curves of 5 to 10 mice per group. Unimmunized controls (squares) were challenged with 100 bacteria.

Mice were immunized with R36a, DPPC:KLH, and EPC:KLH antigens as described in example 4 herein. S. pneumoniae were stained with serum antibodies and the bacteria were analyzed on a FACSCAN as described in example 4, herein.

Mice were immunized with R36a, DPPC:KLH, and EPC:KLH antigens as described in example 4 herein. S. pneumoniae were stained with serum antibodies and the bacteria were analyzed on a FACSCAN as described in example 4, herein.

DETAILED DESCRIPTION

A. Definitions

As used herein, the term "alkyl" refers to a hydrocarbon radical which may be straight chain or branched chain. Preferably, for the present invention, alkyl groups contain 4–20 carbon atoms and more preferably 4–10 carbon atoms. All numerical ranges in this specification are intended to be inclusive of their upper and lower limit. The term "straight chain alkyl" refers to an unbranched alkyl group as defined above.

The term "hapten" as used herein refers to a molecule that is immunogenic when coupled to an immunological carrier. Haptens are generally small molecules that are not capable of eliciting a strong immune response unless coupled to an immunological carrier.

The terms "PC hapten" or "phosphocholine hapten" as used herein refer to a hapten molecule which contains the phosphocholine group.

The terms "PC conjugate" or "phosphocholine conjugate" as used herein refer to a conjugate of a PC hapten with an immunological carrier.

The term "immunological carrier" as used herein refers to a variety of molecules or substances that allow an immune response to be raised against a hapten molecule, when the hapten molecule is attached to the immunological carrier. Immunological carriers include, for example, soluble proteins, polypeptides and polymer molecules. Proteins such as bovine serum albumen and keyhole limpet hemocyanin (KLH) or synthetic polymers such as polylysine are routinely used. The protein or polymer molecules may be immunogenic alone, and antibodies to the carrier molecule may also be produced. In addition to soluble proteins and polymers, immunological carriers also include insoluble substances such as killed microorganisms or fragments thereof. For example, a phosphocholine hapten may be coupled to the surface of killed S. pneumoniae for the purpose of immunizing against infection by this bacteria. The immune response to hapten molecules is described by Berzofsky, J. et al. in Paul, W. E., ed. (1989) Fundamental Immunology, Raven Press, New York, pp.169–208, incorporated herein by reference. Procedures for conjugation of haptens to immunological carriers and for immunizations using the hapten:immunological carrier conjugates are described in Harlow, E. (1988) Antibodies: a Laboratory Manual, Cold Spring Harbor Laboratories, Cold Spring Harbor, N.Y., incorporated herein by reference.

The term "phosphocholine antigen-containing organism" refers to any organism that contains phosphocholine in such a form that anti-phosphocholine antisera will bind to the organism. For example, bacteria such as S. pneumoniae contain phosphocholine as a component of the cell wall. Anti-phosphocholine antisera can be demonstrated to bind S. pneumoniae as shown in example 4 herein.

The term "phosphocholine antigen-containing pathogenic organism" refers to any phosphocholine antigen-containing organism that is pathogenic or which causes disease in an animal.

B. Introduction

The hapten PC is a major antigenic determinant in many pathogenic and nonpathogenic organisms. These pathogenic organisms include both microorganisms and multicellular parasites such as nematode worms and the like. Examples of such bacteria include Streptococcus group O and H bacteria, Streptococcus pneumoniae, various species of Pseudomonas and Proteus Morganii, and Lactobacillus acidophilus. Fungi include Trichoderma, Fusarium and Aspergillus. In addition, there are a variety of parasites, including parasitic nematode worms such as Ascaris and Nippostrongeloides which have phosphocholine antigens. Comprehensive reviews and listings of microorganisms and pathogenic organisms containing PC antigens are described in Potter, M. (1971) Anal. N.Y. Acad. Sci. 190:306 and in Pery, R. et al. (1974) Eur. J. Immunol. 4:637, both incorporated herein by reference.

The PC conjugates described herein may be used to immunize animals against infection by pathogenic organisms containing PC antigens, including those listed above and in Potter, M. supra and in Pery, R. et al., supra. An example of a pathogenic bacterium in which PC is an important antigenic determinant is S. pneumoniae. The S. pneumoniae bacterium is surrounded by a capsule composed of complex carbohydrates. This capsule is the primary virulence factor for S. pneumoniae, providing a mechanism for the bacteria to prevent phagocytosis by macrophages and polymorphonucleocytes. S. pneumoniae also has a cell wall composed of proteins and carbohydrates. The carbohydrate portion of this cell wall has the hapten phosphocholine (PC) as the major antigenic determinant.

Infection of normal mice with unencapsulated variants of S. pneumoniae having an exposed cell wall results in a primary response dominated by IgM and $IgG_3$ anti-phosphocholine (anti-PC) antibodies. These antibodies have a single heavy and light chain idiotype, T15. The remainder of the anti-PC response is composed of two other idiotypes (M167id and M603id) which have the same heavy chain variable region as the T15id, but which have different light chain variable regions. Multiple immunization of mice with the unencapsulated variants of *S. pneumoniae* does not result in a change in the isotype or idiotype distribution of the anti-PC antibody response. Multiple immunizations also do not enhance the secondary response or induce demonstrable affinity maturation, that is, there is no memory response.

The CBA/N mouse strain carries the xid mutation (X-linked immunodeficiency) which results in the clonal deletion of the B cell subsets expressing the Lyb-5+and Ly-1+phenotypes. See Wicker, L. S., et al., (1986) *Curr. Topics Micro. Immunol.* 124:87, incorporated herein by reference. Xid mice, and other mice without these B cell subsets, do not respond to T-independent Type 2 (TI-2) carbohydrate antigens such as dextran, levan, pneumococcal, capsular polysaccharide or PC as it is naturally associated with the cell wall polysaccharide. This B cell defect makes the xid mouse highly susceptible to infection with *S. pneumoniae* and other microorganisms. This phenomenon also makes the xid mouse an effective model for studying the response of an immunocompromised host in *S. pneumoniae* infections.

Passive immunization studies have demonstrated that T15id+antibodies of the IgG1 and IgG3 subclasses are more able to protect xid mice from challenge with *S. pneumoniae* than are IgG2 anti-PC antibodies. Furthermore, all IgG subclasses were more protective than IgM antibodies, while IgA antibodies offered no protection at all.

The standard PC hapten, p-diazophenylphosphocholine (DPPC), when conjugated to protein antigens, induces high affinity phenylphosphocholine- (PPC) specific antibodies in xid mice. These antibodies are not protective against *S. pneumoniae*. In normal mice, the standard DPPC-conjugated protein induces a primary IgM immune response which is dominated by T15-id+anti-PC antibodies (group I), whereas, the secondary IgG response is dominated by group II anti-PPC-specific antibodies. The T15 clone has an affinity 20–40 times higher than the low affinity anti-PC clones which can be generated using the germ-line $V_H1$ gene, and thus, it dominates the primary (1°) immune response. The even higher affinity group II PPC-specific antibodies totally dominate the immune response to DPPC-KLH in xid mice. Thus, the high affinity T15 and group II responses obscure the small low affinity group I response in xid mice and effective immunity to PC-containing organisms such as *S. pneumoniae* is not developed.

In contrast to DPPC, PC conjugates such as p-nitrophenyl-6-(O-phosphocholine)-hydroxyhexanoate (EPC) are capable of eliciting a PC-specific response in xid mice, when coupled to an appropriate immunological carrier. See examples 1–4 herein. Specifically, these haptens, when coupled to an appropriate carrier, can rescue a group I anti-PC response in xid mice. In EPC-conjugated proteins, the PC hapten is separated from the protein backbone by a 9-carbon linear spacer. This linear PC-spacer arrangement allows the immune response in both xid and normal mice to remain PC-specific even after repeated immunizations. Comparison of the ability of EPC-KLH conjugates and DPPC-KLH conjugates to generate PC-specific immune response in xid mice (see examples 1–4 herein), demonstrates that a linear straight chain alkyl linker is effective in eliciting such a response.

Conjugates such as EPC-KLH succeed in inducing a PC-specific response in xid mice because the PC moiety is extended away from the carrier protein by a long straight-chain carbon spacer, whereas in the conventionally used DPPC antigen, the PC is directly linked to a large immunodominant phenyl ring structure. This dominant phenyl ring causes the response to DPPC-KLH to undergo affinity maturation via the selective amplification of high affinity group II PPC-specific antibodies which do not use the $V_H1$ gene to encode their H-chains. See Wicker, et al. (1982) *J. Immunol.* 131:2468 and Wicker, et al. (1982) *J. Immunol.* 129:950. In contrast, PC conjugates such as EPC with straight chain linkers allow for the selection and maturation of presumably low affinity PC-specific (group I) clones that have not been clonally deleted in the xid mice. Thus, the PC analogues described herein with straight chain alkyl linker groups can be used as a vaccine to protect immunocompromised animals from infection with *S. pneumoniae* and other PC antigen-containing organisms.

C. PC conjugate compositions

The compounds of the present invention are PC conjugates which are capable of eliciting an immune response to PC when administered to an animal. These PC conjugates are represented by formula I:

The X group in formula I is an —O—, —S—, —CH$_2$—, or —NH—group.

The Y group in formula I is a straight chain alkyl group. Straight chain alkyl groups of a variety of lengths may be used. Preferably the straight chain alkyl group is 4–20 carbon atoms and more preferably 4–10 carbon atoms in length.

The NH group of the amide linkage in the above formula is contributed from an amino group from the immunological carrier. For example, the NH group may be contributed by the ε amino group of a lysine residue of a protein or polypeptide.

The R group of formula I is the remainder of the immunological carrier. As described above, the immunological carrier may be a soluble protein such as bovine serum albumin (BSA) or keyhole limpet hemocyanin (KLH) proteins. Other soluble naturally occurring proteins or polypeptides known to those of skill in the art may also be used. R also includes polymers of amino acids or amino acid analogues, for example synthetic polylysine polymers. R also includes a variety of other substances including killed microorganisms or fractions thereof.

D. Synthesis of PC Haptens and Conjugation of PC Haptens to Proteins or Polymers Phosphocholine esters including p-nitrophenyl-6-(O-phosphocholine)hydroxyhexanoate (EPC) are synthesized as described by Spande, et al. (1980) *J. Org. Chem.* 45:3081–3084, which is incorporated herein by reference.

Analogues of EPC in which the length of the straight chain alkyl group (the "Y" group in formula I) is varied are synthesized by modifications of the procedure of Spande, et al. In Spande, et al., tert-butyl 6-hydroxyhexanoate was used to prepare EPC using the PC ester synthesis method described in Hirt, R. et al. 1958) *Pharm. Acta Helv.* 33:349 with the hydrolysis modification described in Cheseboro, B, et al., supra and the aminolysis modification described in Eibl, H., et al. (1967) *Justus Liebegis Ann. Chem.* 709: 226. There are a variety of different starting compounds that can be used by one of skill in the art to replace the tert-butyl 6-hydroxyhexanoate in the above synthesis or in modifications of the above synthesis to yield PC esters of varying chain length of the alkyl group represented by "Y" in the above formula.

Analogues of EPC in which the "X" group of formula I is varied as described above are synthesized by modifications of the method of Spande, et al., which are known to those of skill in the art.

EPC and its analogues which contain 6-para-nitrophenyl or other leaving groups known to those of skill in the art, may be conjugated to amino groups of proteins, polypeptides, polymers or other immunological carriers by a variety of methods. For example, EPC or EPC analogues containing 6-para-nitrophenyl may be conjugated to proteins using the method described in example 1 herein. Variations in the conjugation conditions described in example 1 known to those of skill in the art may also be employed to effect conjugation to amino groups present on immunological carriers.

As described in Spande, et al., supra 6-(O-phosphocholine)hydroxyhexanoate is an intermediate in the synthesis of EPC. 6-(O-phosphocholine)hydroxyhexanoate, or analogues thereof with alkyl groups of varying length, may be used to synthesize a variety of PC analogues that may be readily conjugated to immunological carriers. A variety of activated esters, for example, may be synthesized from 6-(O-phosphocholine)hydroxyhexanoate. Specific examples of the preparation of these activated esters include the reaction of 6-(O-phosphocholine)hydroxyhexanoate with N-hydroxysuccinamide, with N-methyl flouropyridinium tosylate, or with 4,6-diphenylthieno[3,4-d]-1, 3dioxol-2-one 5,5 dioxide. See (1966) Chem. BCR 99:110, (1976) *Chem. Lett.* (Jap.) 303, (1976) Angew Chem Int. Ed. Eng. 15:444, all incorporated herein by reference. These PC compounds can all be readily coupled to amino groups present on immunological carriers using methods known to those of skill in the art.

E. Testing of Conjugates

1. Elicitation of an immune response

The PC conjugates synthesized as described above are tested for their ability to elicit protective antibodies to PC when the conjugates are administered to mammals. A variety of model systems known to those of skill in the art may be used to establish the ability of the conjugates to raise antibodies specific to PC and to provide immunoprotection to the host. These animal model systems generally use three types of experimental protocols to establish immunoprotection, which are passive transfer of protective antibodies, adoptive transfer of white blood cells, and direct in situ challenge by pathogenic organisms in an appropriate immunized animal. Examples of these three types of protocols in the xid mouse are shown in examples 2 and 3 herein.

Animal models for immunocompromised conditions are particularly relevant to the testing of the above conjugates, since, as described above, there are large patient groups that are immunodeficient in their ability to respond to PC antigens. Use of a preferred model system for testing the PC conjugates for their ability to elicit a PC-specific response is described in detail in example 2 herein. In particular, xid mice described in example 1 may be used to test the ability of the PC conjugate to elicit anti-PC antibodies in an immunocompromised animal.

Antisera from animals immunized with the PC conjugates may be tested for their ability to bind *S. pneumoniae* or other microorganisms containing PC in their capsids or cell membranes. Since production of antibodies capable of binding the bacteria is necessary for effective vaccination, the production of antibodies with this capability may be used to test the conjugates for their desirability for use in a vaccine. A variety of bacterial strains may be used, including the WU-2 strain of *S. pneumoniae*, described in example 3 herein. The antisera from immunized animals, including, for example, the xid mouse, may be tested as described in example 4 herein.

2. pneumoniae challenge in normal and xid mice

The PC conjugates described above may be tested for their ability to immunize mammals against infections by bacteria containing PC antigens in their cell walls. The animal model systems described above may be used for this purpose. A variety of bacteria may be used to challenge the animals in these systems including a number of strains of *S. pneumoniae* known to those of skill in the art. The xid mouse model described in example 2 herein is particularly useful in evaluation of the PC conjugates. Immunizations and challenge with *S. pneumoniae* may be carried out, for example, as described in example 3 herein.

F. Pharmaceutical Compositions and Administration of Vaccines

The PC conjugates of the invention are useful in vaccines and in immunization protocols for prevention of infection in animals by pathogenic organisms from bacteria containing PC antigens. As described above, *S. pneumoniae*, a bacterium causing pneumonia, is a medically important example of such an organism.

Pharmaceutical compositions of the invention are suitable for use in a variety of drug delivery systems. Pharmaceutically acceptable carriers and formulations for use in the present invention are found in *Remington's Pharmaceutical Sciences*, Mack Publishing Company, Philadelphia, PA, 17th ed. (1985), which is incorporated herein by reference. For a brief review of methods for drug delivery, see, Langer, *Science* 249:1527–1533 (1990), which is incorporated herein by reference.

The PC conjugates of the present invention can be used in pharmaceutical vaccine compositions that are useful for administration to mammals, particularly humans. These compositions comprise the PC conjugates and pharmaceutically acceptable carriers. These compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of pharmaceutically acceptable aqueous carriers may be used, e.g., water, buffered water, 0.4% saline, 0.3% glycine hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the PC conjugates are preferably supplied in finely divided form along with a surfactant and propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides, may be employed. A carrier can also be included, as desired, as with, e.g., lecithin for intranasal delivery.

The PC conjugates of the invention are used prophylactically as vaccines. The vaccines of the invention contain as an active ingredient a PC conjugate. Useful pharmaceutically acceptable carriers are well known in the art, and include, for example, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

Vaccine compositions containing the PC conjugates of the invention are administered to a patient to elicit a protective immune response against the polypeptide. A "protective immune response" is one which prevents infection by a bacterium containing PC in its cell wall. An amount sufficient to accomplish this is defined as an "immunogenically effective dose." Amounts effective for this use will depend on, e.g., the PC conjugate composition, the manner of administration, the weight and general state of health of the patient, and the judgment of the prescribing physician. For example, the present vaccine may be administered to the groups of patients who do not respond well to current vaccines. These patients include those who are immunocompromised in their ability to respond to other PC immunogens. Dosages, formulations and administration schedules may vary in these patients compared to normal individuals. In general, dosages range for the initial immunization from about 10 μg to about 1,000 mg of the PC conjugate for a 70 kg patient, followed by boosting dosages of from about 10 μg to about 1,000 mg of the PC conjugate, pursuant to a boosting regimen over weeks to months depending upon the patient's response and condition. The patient's response can be measured, for example, by measuring anti-PC antibodies present in the patients blood at intervals after the initial immunization.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

EXAMPLES

Example 1

Synthesis and Conjugation of PC Haptens Aminophenylphosphocholine (APPC) and p-nitrophenyl-6-(O-phosphocholine)hydroxyhexanoate (EPC) were synthesized as described by Chesebro, B. and Metzger, H. (1972) *Biochem.* 11:776 and by Spande, T. F., supra, respectively. APPC was converted to DPPC as previously described by Chesebro and Metzger, supra. The DPPC (30:1 molar input ratio) and EPC haptens were conjugated to keyhole limpet hemocyanin (KLH) (100,000 used as MW) dissolved in borate buffered saline (BBS), pH 8.5 at 10 mg/ml. EPC was dissolved in dry acetonitrile (100 mg/ml) just prior to adding it to the KLH. Hapten and KLH were mixed overnight at 4° C. and then dialyzed to remove unbound hapten and the released p-nitrophenylate. Due to the fact that the p-nitrophenyl ester linkage of the EPC hapten is readily hydrolyzed by $H_2O$, it was not possible to correlate the release of p-nitrophenylate during our conjugation procedure with protein bound phosphate, and a wide range of PC/KLH (9:1 to 35:1) has been obtained using the same 100:1 molar input of EPC. Phosphate bound to protein was estimated according to the method described in Ames, B. N., et al. (1960) *J. Biol. Chem.* 235:769.

Example 2

Demonstration of a PC-specific immune response induced in xid mice by EPC-KLH.

a. Elicitation of PC-specific antibodies

It has been difficult to induce a response to PC in xid mice because they do not respond to the natural TI-2 form of PC located on the techoic acid of the cell walls of *S. pneumoniae*. When immunized with DPPC-KLH, the standard TD form of PC, xid mice produce mainly IgG1 anti-PPC-specific antibodies. The immunodominant phenyl ring of the DPPC selects high affinity group II B cell clones for expansion, and thus, prevents expansion of the very low affinity group I anti-PC-specific B cells. EPC-KLH, which lacks the phenyl ring was coupled to KLH according to the above procedure at several different hapten input ratios.

CBA/N,(CBA/N×DBA/2)F1, and BALB/c mice were obtained from the Small Animal Facility, NIH, Bethesda, MD. Breeding pairs of the consomic xid C.CBA/N mice were obtained from Dr. Carl Hansen, Division of Veterinary Medicine, National Institutes of Health, Bethesda, MD. These mice were derived as previously described for the C3.CBA/N strain and were maintained in our colony by brother-sister mating. See Gray, B. M., et al. (1983) *J. Clin, Micro.* 18:1102–1107. Mice were used between 2 and 6 months of age.

In general, mice were immunized i.p. with 200 μg of the EPC conjugates prepared as described above in CFA (Difco, Detroit, MI) and bled on day 7 for primary response serum and boosted with another 200 μg of antigen in IFA on day 14 followed by bleeding on day 21 to obtain 2° response serum. Phenotypically normal CDF1 female and immune defective CDF1 male xid mice were immunized and boosted according to the above schedule, and their serum was analyzed at 7 days after the secondary immunization. The anti-PC response is shown in Table 1 below.

TABLE 1

Serum Anti-PC Response of (CBA/N × DBA/2) F1 Mice Immunized with 6-(O-phosphocholine) hydroxyhexanoate-Conjugated KLH

| Group | Conjugation Ratio‡ | μg Anti-PC Antibody/ml Serum@ | | | |
|---|---|---|---|---|---|
| | | IgM | | IgG | |
| | | Primary | Secondary | Primary | Secondary |
| CDF1 ♂ | 20:1 | 333 | 117 | 965 | 785 |
| CDF1 ♂ | 50:1 | 105 | 150 | 900 | 2017 |
| CDF1 ♂ | 100:1 | 70 | 273 | 1360 | 3967 |
| CDF1 ♀ | 20:1 | 2 | <1 | 5 | 69 |
| CDF1 ♀ | 50:1 | 5 | 2 | 37 | 218 |
| CDF1 ♀ | 100:1 | 8 | 3 | 17 | 580 |

‡This represents the molar input ratio of hapten to KLH. Based on the phosphate assay, the 100:1, 50:1, and 20:1 had 9, 4.5. and 2 phosphate groups per KLH. The antigen with a 20:1 input was estimated by extrapolation of?the standard curve.
@Serum anti-PC antibody levels were determined as described in Banerji, B., et al. (1982) J. Inununol. 128:1603, using standard curves generated with affinity purified T15-id + IgM (HPCM2) and IgG1 (HPCG14) antibodies. See Gearhart, P.J., et al. (1981) Mature 291:29.

EPC-KLH induced good 1° and 2° anti-PC responses in the normal F1 ♀ mice at all ratios of EPC/KLH tested. The EPC-KLH at a 20:1 input ratio induced the highest 1° IgM response while the antigen with a 100:1 input ratio induced the highest 1° and 2° IgG responses and the highest 2° IgM response. Like other PC-antigens, EPC-KLH induced very low but detectable 1° responses in the xid CDF1 ♂ mice at all ratios of hapten/carrier. The 100:1 EPC-KLH was much better than the 20:1 at inducing 2° IgG responses; however, this response was still 6 fold lower than that of the normal F1 ♀. Since the 100:1 EPC-KLH induced the best response in the immune defective CDF1 ♂ mice, all subsequent experiments were conducted using antigen produced at this coupling ratio.

It was of particular interest to analyze the response in the BALB/c consomic C.CBA/N strain of xid mice as well as the two parental strains used to derive them. BALB/c, C.CBA/N and CBA/N mice were immunized twice as described above with either EPC-KLH or DPPC-KLH and their 1° day 7 and 2° day 21 serum responses analyzed. See table 2 below.

TABLE 2

Serum Anti-PC Response of BALB/c, C.CBA/N and CBA/N Mice to PC-KLH*

| Group | Antigen | μg Anti-PC Antibody/ml Serum | | | |
|---|---|---|---|---|---|
| | | IgM | | IgG | |
| | | Primary | Secondary | Primary | Secondary |
| BALB/c | DPPC-KLH | 348 | 143 | 26 | 333 |
| BALB/c | EPC-KLH | 76 | 192 | 41 | 262 |
| C.CBA/N | DPPC-KLH | 15 | 23 | 4 | 351 |
| C.CBA/N | EPC-KLH | 8 | 9 | <1 | 69 |
| CBA/N | DPPC-KLH | 6 | 10 | <1 | 445 |
| CBA/N | EPC-KLH | 10 | 2 | <1 | 39 |

*Mice were immunized and bled as described above and the serum assayed as in Table 1 and Banjeri, B., et al., supra.

As was seen for the immune defective CDF1 ♂ mice in Table 1, EPC-KLH induced a significant 2° IgG1 response in both the parental CBA/N and consomic C.CBA/N xid mice. The IgG response to DPPC-KLH is always greater than the response induced by EPC-KLH.

b. Demonstration of a PC-specific immune response to EPC-KLH in xid mice.

To characterize the idiotypic and isotypic nature of the immune response induced by EPC-KLH, the spleen cells from mice primed with the 100:1 and 20:1 EPC-KLH antigens in table 1 were transferred intravenously to irradiated (800 Rad) CDF1 ♂ recipients along with 25 μg of the same antigen as was used for priming. Adoptive transfer assays were performed using 20 ×10⁶ spleen cells and irradiated syngeneic recipients as previously described. See Wicker, L. S. G., et al. (1982) J. Immunol. 129:950.

Splenic plaque forming cells (PFC) were detected 7 days after adoptive transfer, and PFC idiotype (id) and hapten inhibition assays were performed as previously described. See Wicker, L. S. G., et al., supra. Serum IgM and IgG anti-PC antibody levels were elucidated by RIA as previously described. See Banerji, B., et al. (1982) J. Immunol. 128:1603. The results are shown in table 3 below.

TABLE 3

Effect of Epitope Density on the Adoptive Transfer Response to
6-(O-phosphocholine) hydroxyhexanote-Conjugated KLH*

| Group | Conjugation Ratio‡ | IgM | | | | IgG1 | | | |
|---|---|---|---|---|---|---|---|---|---|
| | | PFC/Spleen@ | % Inhibition | | | PFC/Spleen | % Inhibition | | |
| | | | T15-id | PC | NPPC | | T15-id | PC | NPPC |
| CDF1 ♂ | 100:1 | 86,611 | 84 | 99 | 100 | 91,389 | 54 | 99 | 99 |
| | 20:1 | 22,611 | 50 | 95 | 98 | 22,049 | 16 | 94 | 98 |
| CDF1 ♀ | 100:1 | 3,287 | 10 | 99 | 99 | 34,551 | 0 | 89 | 100 |
| | 20:1 | 2,910 | 54 | 97 | 98 | 3,967 | 20 | 92 | 100 |

*Mice were immunized as described in Table 1. Adoptive transfer assays were conducted 6 weeks after immunization.
‡See Table 1.
@PFC assays and inhibition assays were performed as previously described.

The most striking result in Table 3 is the fact that virtually all the PFC induced with EPC-KLH are PC-inhibitable. The B cells from mice primed with the 100:1 conjugated EPC-KLH responded better in adoptive transfer than those from mice primed with EPC-KLH conjugated at 20:1. The greatest difference in response was in the IgG1 isotype of the immune defective xid males. As expected, the IgM response of the phenotypically normal CDF1 ♀ mice was dominated by the T15-id. In 4 experiments with CDF1 ♀ mice primed with EPC-KLH (100:1), the % T15-id⁺IgM PFC ranged from 54 to 84%, whereas the small IgM PFC response of CDF1 ♂ mice ranged from 10 to 50% T15-id⁺. On the other hand, the IgG1 response of both CDF1 ♂ and ♂ mice was not dominated by the T15-id. Immune defective CDF1 ♀ mice primed with 100:1 EPC-KLH always had <12% T15-id⁺ IgG1 PFC while the CDF19 mice had an average of 28% T15-id⁺IgG1 PFC (range 8 to 54%). The IgG2, IgG3 and IgA responses of the CDF1 ♀ mice were always much lower than the IgG1 adoptive transfer response and have therefore not been presented; however, when there were enough PFC to conduct inhibition assays, the responses were PC-inhibitable and generally dominated by the T15-id. Immune defective CDF1 ♂ mice produced <1000 IgG2, IgG3 or IgA PFC and these were not phenotyped.

The PFC response induced by EPC-KLH in xid mice was compared to that induced by DPPC-KLH in xid mice in adoptive transfer assays. As was seen in Table 3, the vast majority of PFC in the adoptive transfer response to EPC-KLH were PC-inhibitable. A 2° IgG1 response to DPPC-KLH is generally not PC-inhibitable; yet even after the 3rd exposure to EPC-KLH, the xid response was about 90% PC-inhibitable (See Table 3). The data in Table 4, below, show a direct comparison of the 3° immune response of CDF1 mice to EPC-KLH and DPPC-KLH. For the experiment shown in table 4, mice were primed 2x with antigen on day 0 and day 14 and spleen cells adoptively transferred 6 weeks later.

TABLE 4

Adoptive Transfer Response of (CBA/N × DBA/2)F1 Mice to Phosphocholine*

| Group | Conjugation Ratio‡ | IgM | | | | IgG1 | | | |
|---|---|---|---|---|---|---|---|---|---|
| | | PFC/Spleen | % Inhibition | | | PFC/Spleen | % Inhibition | | |
| | | | T15-id | PC | NPPC | | T15-id | PC | NPPC |
| CDF1 ♂ | DPPC-KLH | 22,948 | 78 | 97 | 99 | 135,895 | 21 | 31 | 92 |
| CDF1 ♂ | EPC-KLH | 14,291 | 54 | 91 | 99 | 190,745 | 23 | 98 | 100 |
| CDF1 ♀ | DPPC-KLH | 2,124 | 24 | 27 | 60 | 35,223 | 17 | 17 | 84 |
| CDF1 ♀ | EPC-KLH | 2,698 | 50 | 95 | 99 | 36,273 | 12 | 84 | 100 |

*Immunizations, adoptive transfer assays, and PFC assays were as described in Tables 1 & 3.

As previously shown for DPPC-KLH, the IgM response of normal CDF1 ♀ mice is dominated by T15-id⁺PC-inhibitable PFC whereas the IgG1 response is primarily T15-id⁺, and PC-non-inhibitable as are both the IgM and IgG1 responses of immune defective CDF1 ♂ mice. On the other hand, EPC-KLH induces predominantly PC-inhibitable IgM and IgG PFC responses in both the normal CDF19 ♀ and defective ♂ mice, and the IgG portion of this response is not dominated by the T15-id.

The PC-inhibitable character of the response to KLH-EPC was also determined in other strains of xid mice by using the adoptive transfer assay.

TABLE 5

Adoptive Transfer Response of BALB/c and C.CBAN Mice to Phosphocholine*

| | | Isotype | | | | | | | |
|---|---|---|---|---|---|---|---|---|---|
| | | IgM | | | | IgG1 | | | |
| | Conjugation | | % Inhibition | | | | % Inhibition | | |
| Group | Ratio‡ | PFC/Spleen | T15-id | PC | NPPC | PFC/Spleen | T15-id | PC | NPPC |
| EXP #1 | | | | | | | | | |
| BALB/c | DPPC-KLH | 95,477 | 79 | 97 | 93 | 181,969 | 15 | 38 | 98 |
| BALB/c | EPC-KLH | 116,483 | 83 | 99 | 99 | 326,530 | 16 | 99 | 100 |
| C.CBA/N | DPPC-KLH | 2,592 | — | — | — | 194,817 | 22 | 28 | 93 |
| C.CBA/N | EPC-KLH | 1,321 | — | — | — | 155,693 | 4 | 75 | 100 |
| EXP #2 | | | | | | | | | |
| BALB/c | DPPC-KLH | 197,293 | 82 | 96 | 99 | 203,308 | 10 | 47 | 98 |
| BALB/c | EPC-KLH | 135,671 | 80 | 98 | 99 | 287,382 | 37 | 96 | 100 |
| C.CBA/N | DPPC-KLH | 5,990 | 4 | 2 | 76 | 98,904 | 21 | 22 | 92 |
| C.CBA/N | EPC-KLH | 5,095 | 43 | 66 | 98 | 114,169 | 0 | 65 | 100 |

*Immunizations, adoptive transfer assays, and PFC assays were as described in Tables 1 & 3. Recipients were irradiated with 400 Rad. prior to transfer.

As was demonstrated in table 2 above, EPC-KLH induced a significant 2° IgG1 response in both the parental CBA/N and consomic C.CBA/N xid mice. The IgG response to DPPC-KLH is always greater than the response induced by EPC-KLH. However, as seen in Table 5, the major part of the IgG response to DPPC-KLH was not PC-inhibitable, whereas, the response to EPC-KLH was predominantly PC-specific in both the normal BALB/c and C.CBA/N xid mice. Again, the IgG1 responses induced by both DPPC-KLH and EPC-KLH were primarily T15-id–, as were the small IgM responses in the C.CBA/N mice. As expected, the IgM response of the BALB/c mice to both antigens was predominantly T15-id+.

Thus, the EPC-KLH succeeds in inducing a PC-specific response in xid mice. When xid mice were immunized multiple times with EPC-conjugated KLH, all strains tested responded by producing significant levels of IgG1, T15-id–, PC-specific antibodies. The small IgM response induced in xid mice by EPC-KLH was also PC-specific, but usually contained a substantial T15-id+ component. Normal mice injected with EPC-KLH produced the expected T15-id+ IgM response and an IgG1 response which was primarily T15-id–. However, this 2° IgG response was predominantly PC-inhibitable, unlike the typical PC-non-inhibitable response induced by DPPC-KLH. See tables 4 and 5. This result is significant, since it is known that anti-PC specific antibodies of the IgG1 subclass can provide protection to xid mice in passive protection studies. In contrast, the 2° immune response induced in xid mice by the traditional DPPC-KLH antigen was dominated by IgG1 PPC-specific (group II) antibodies. See tables 4 and 5. These results are thus supportive of the results shown below demonstrating the EPC-KLH, but not DPPC-KLH, is capable of consistently protecting xid mice from challenge with S. pneumoniae.

The EPC-KLH apparently succeeds in inducing a PC-specific response in xid mice because the PC moiety is extended away from the carrier protein by a long straight-chain carbon spacer, whereas in the conventionally used DPPC antigen, the PC is directly linked to a large immunodominant phenyl ring. This dominant phenyl ring causes the response to DPPC-KLH to undergo affinity maturation via the selective amplification of high affinity group II PPC-specific antibodies which do not use the $V_H1$ gene to encode their H-chains. In contrast, EPC allows for the selection and maturation of presumably low affinity PC-specific (group I) clones that have not been clonally deleted in the xid mice.

Example 3

Protection of xid mice against S. pneumoniae following immunization with EPC-KLH C.CBA/N mice were immunized twice with 200 μg of EPC-KLH as described above. Seven days after the 2° immunization (day 21) these mice and unimmunized controls were challenged with various doses of virulent S. pneumoniae according to the following protocol. The WU-2 strain of Type 3 Streptococcus pneumoniae was obtained from Dr. David Briles, University of Alabama, Birmingham, Ala. WU-2 is a virulent Type 3 strain of S. pneumoniae previously used for challenge experiments in mice and is maintained in glycerol stocks at −70° C. until needed, with frequent passage through mice to maintain virulence. Bacteria were grown in Todd Hewitt Broth supplemented with 0.5% yeast extract for 4–6 hr., centrifuged at 4000 ×g for 10 min., and the pellet resuspended in PBS. The O.D.420nm was then determined (O.D. 1=3×108 CFU/ml) and the bacteria diluted in PBS to 10 to $10^4$ bacteria/0.2 ml for i.p. challenge. Diluted bacteria were plated on blood agar plates and grown overnight to determine the exact number of viable bacteria. Five to 10 animals were assigned to each group and immunized on day 0 and day 14 as described above. Challenge with S. pneumoniae occurred on day 21, and survival curves were plotted an percent alive vs. time.

Figure 1:
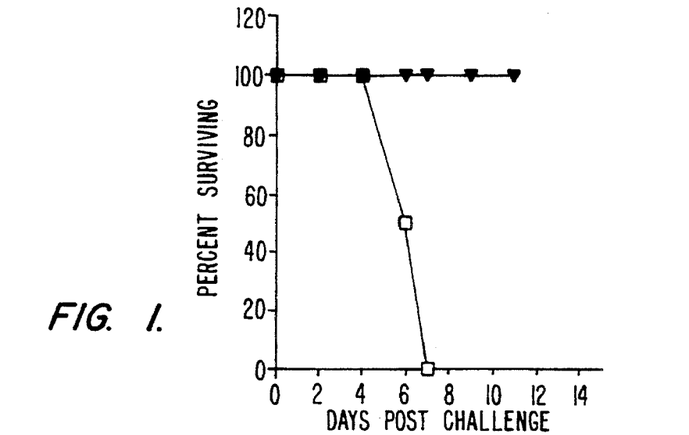
FIG. 1. Protection of C.CBA/N mice against *Streptococcus pneumoniae* following immunization with EPC-KLH.

The data shown in FIG. 1 demonstrate that mice immunized with EPC-KLH were resistant to challenge with $10^4$ bacteria, whereas the unimmunized control all died following challenge with as few as 10 bacteria.

EPC-KLH was then compared with DPPC-KLH for the ability of the conjugates to protect both normal and xid mice from challenge with S. pneumoniae. Normal and xid mice were immunized with EPC-KLH and DPPC-KLH as described above. Preparations of the WU-2 bacteria, described above, were then prepared for the challenge experiments as follows. WU-2 bacteria were plated on trypticase soy agar (TSA) supplemented with 5% Sheep blood (GIBCO) from the frozen stocks and incubated for 14 hours at 37° C. Bacteria were transferred to fresh Todd Hewitt Broth supplemented with 0.5% yeast extract (THB) media and incubated 4–6 hours at 37° C. Bacteria were centrifuged at 4000 ×g for 10 minutes at 4° C. and the pellet resuspended in PBS. An O.D.420$_{nm}$ reading was taken (an OD of 1–3×10$^8$ CFU/ml (5)) and the number of bacteria adjusted to the concentration needed for the challenges. All bacteria for challenges were plated after challenge to confirm the number of CFU/ml given to each animal.

The immunized mice were randomly assigned to challenge groups and challenged 7 days after their second dose of antigen. Animals were challenged i.p. with serial 10-fold increments of the WU-2 bacteria, survival curves plotted, and changes in the LD$_{50}$ values calculated. For the passive transfer protection assays, purified antibody preparations were injected intraperitoneally into naive, xid recipients and challenged at the same time as antibody transfer with *S. pneumoniae* in serial 10-fold increments. Survival curves were then plotted and LD50 values calculated to determine protective efficacy of the antibody treatments.

Figure 2A:
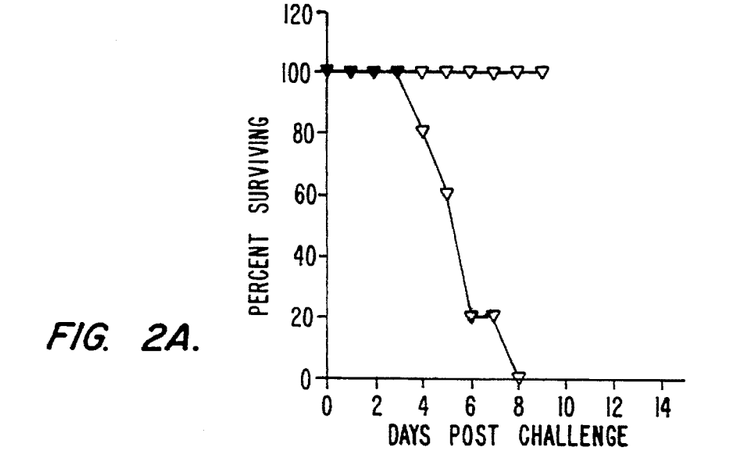
FIG. 2A. Protection of BALB/C mice against *Streptococcus pneumoniae* following immunization with DPPC:KLH.
Figure 2B:
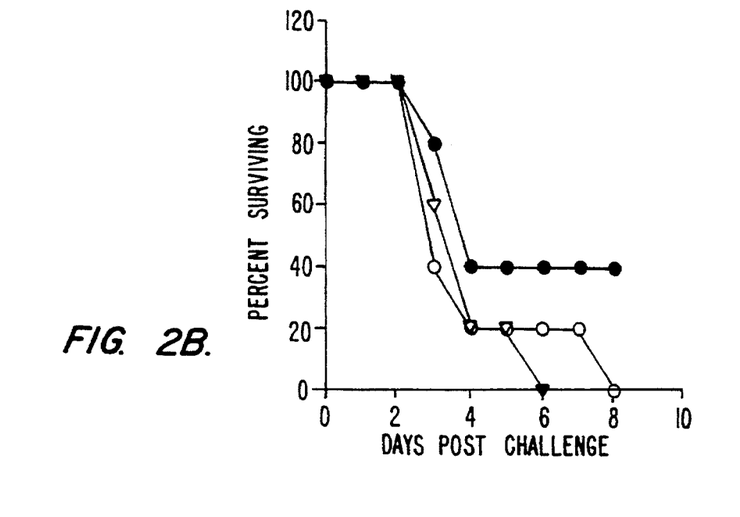
FIG. 2B. Protection of C.CBA/N xid mice against *Streptococcus pneumoniae* following immunization with DPPC:KLH.

Using the above protocol, immunization with DPPC:KLH was shown to protect normal but not xid mice. BALB/c and xid mice were immunized twice with DPPC:KLH and challenged as described above with the virulent WU-2 strain. See FIGS. 2A and 2B. Normal BALB/c mice were totally protected up to 10$^4$ CFU per mouse, with an LD$_{50}$ of between 10 and 100 CFU for the unimmunized controls. See FIG. 2A. In contrast, DPPC:KLH immunization failed to increase the LD$_{50}$ in the xid mice, although there were random animals which survived the challenge procedure. See FIG. 2B. Thus, using the DPPC:KLH TD form of PC in xid mice is not sufficient to vaccinate the immunodeficient animals against *S. pneumoniae* infection.

Figure 3A:
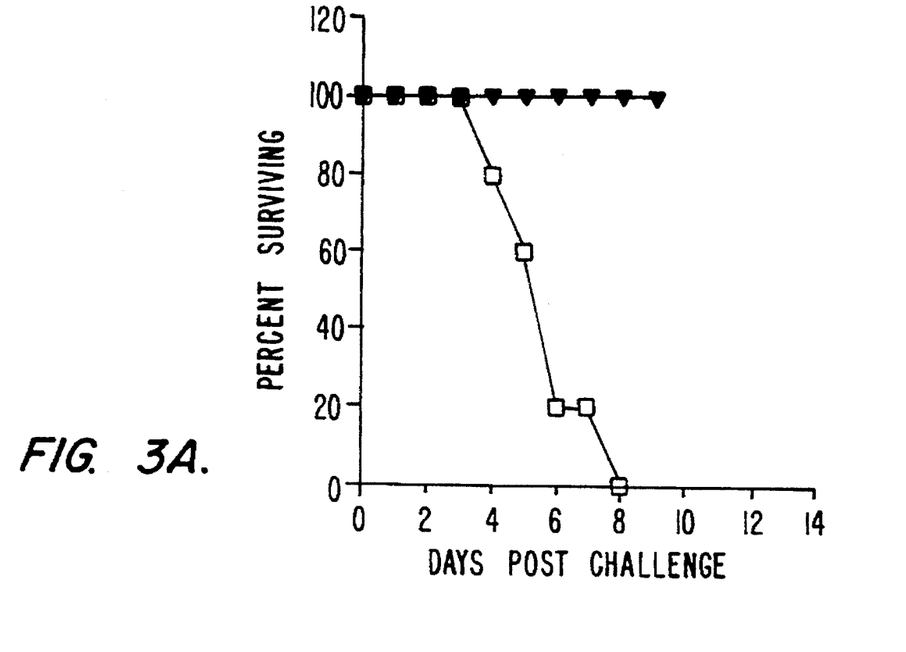
FIG. 3A. Protection of BALB/C mice against Streptococcus pneumoniae following immunization with EPC:KLH.
Figure 3B:
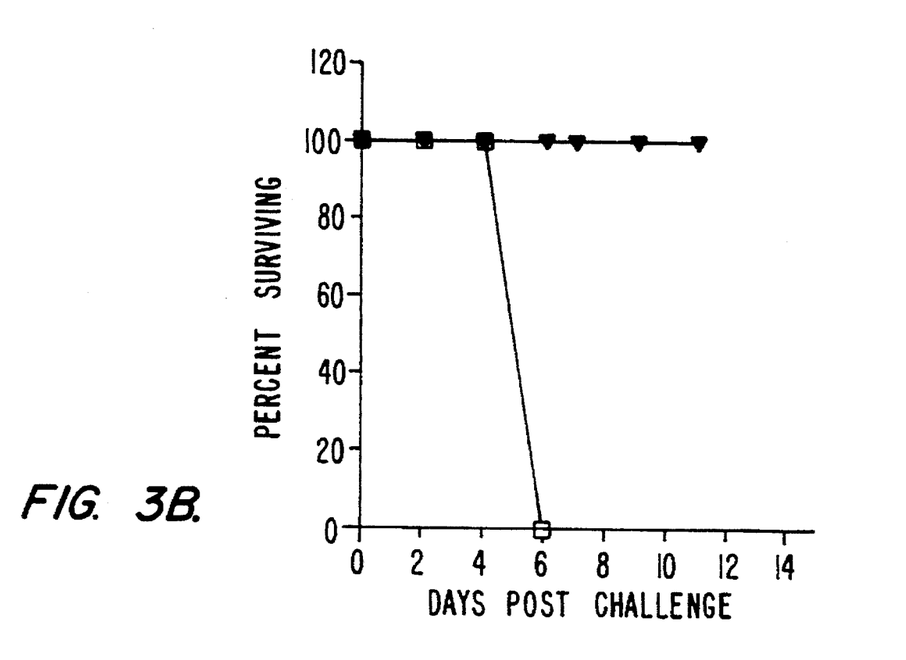
FIG. 3B. Protection of C.CBA/N xid mice against Streptococcus pneumoniae following immunization with EPC:KLH.

In contrast to the above results with DPPC-KLH, immunization with EPC:KLH protects xid mice as well as normal mice. DPPC:KLH induces the Group II, PPC specific antibodies due to the presence of the immunodominant phenyl rings from the DPPC and the tyrosine residues it attaches to on the KLH carrier. EPC, on the other hand, attaches to the lysine side chains of the KLH and gives a 10 atom nonimmunogenic spacer chain between the carrier KLH molecule and the PC moiety. BALB/c and xid mice were immunized with EPC:KLH and challenged with the virulent WU-2 bacterial strain as described above. Both the normal BALB/c and C.CBA/n xid mice were totally protected against challenge doses of the WU-2 up to 10$^4$ CFU per mouse. See FIGS. 3A and 3B.

Example 4

Ability of anti-PC antibodies induced by EPC-KLH to bind *S. pneumoniae* bacteria Immunoprotection of the mice challenged with *S. pneumoniae* was expected to be positively correlated with the ability of antisera from these mice to bind to the bacterium. Specifically, anti-PC antibodies would only be capable of protecting recipient animals if they could be demonstrated to bind to intact bacteria.

Serum antibodies produced after immunization with the three different antigenic forms of PC, the R36a, DPPC:KLH and EPC:KLH were tested for their ability to bind to the intact WU-2 bacteria as measured by FCM analysis. The DPPC:KLH and EPC:KLH conjugates were prepared and used for immunizations as described above. Heat inactivated and lyophilized R36a (a Type 2, unencapsulated and avirulent strain of *S. pneumoniae* which functions as a TI source of PC, a gift from Dr. Jan Cerny, Department of Microbiology, University of Maryland at Baltimore) was administered i.p. as a reconstituted vaccine in phosphate buffered saline (PBS) or in adjuvant at 50 µg per mouse. Animals received antigen on day 0 and were boosted on day 14, and bleeds performed at day 7 for primary responses and day 21 for secondary responses.

Methods for flow cytometric analysis (FCM) of bacteria were as follows. Bacteria were grown as previously described for the protection assays. The bacteria were harvested and washed 2 times in PBS at 4,000× g for 10 minutes. Bacterial cell numbers were adjusted as previously described to stain 2×10$^6$ bacteria in O.1ml per tube. Immune sera, hybridoma antibodies generated against EPC, and PC and NPPC specific control antibodies were added at 1 µg per 10$^6$ cells and incubated on ice for 30 minutes. Excess antibody was washed off and the bacteria were fixed in 2% paraformaldehyde for analysis if the stains were direct. For indirect staining, goat anti-mouse Ig FITC (Fisher Biotech) was added at 1 µg per 10$^6$ bacteria and incubated for 30 minutes on ice. Excess antibodies were then washed off and the bacteria fixed for analysis. FCM analysis was performed an a Becton Dickinson FACScan flow cytometer using the Lysis II software package for acquisition and analysis.

Figure 4:
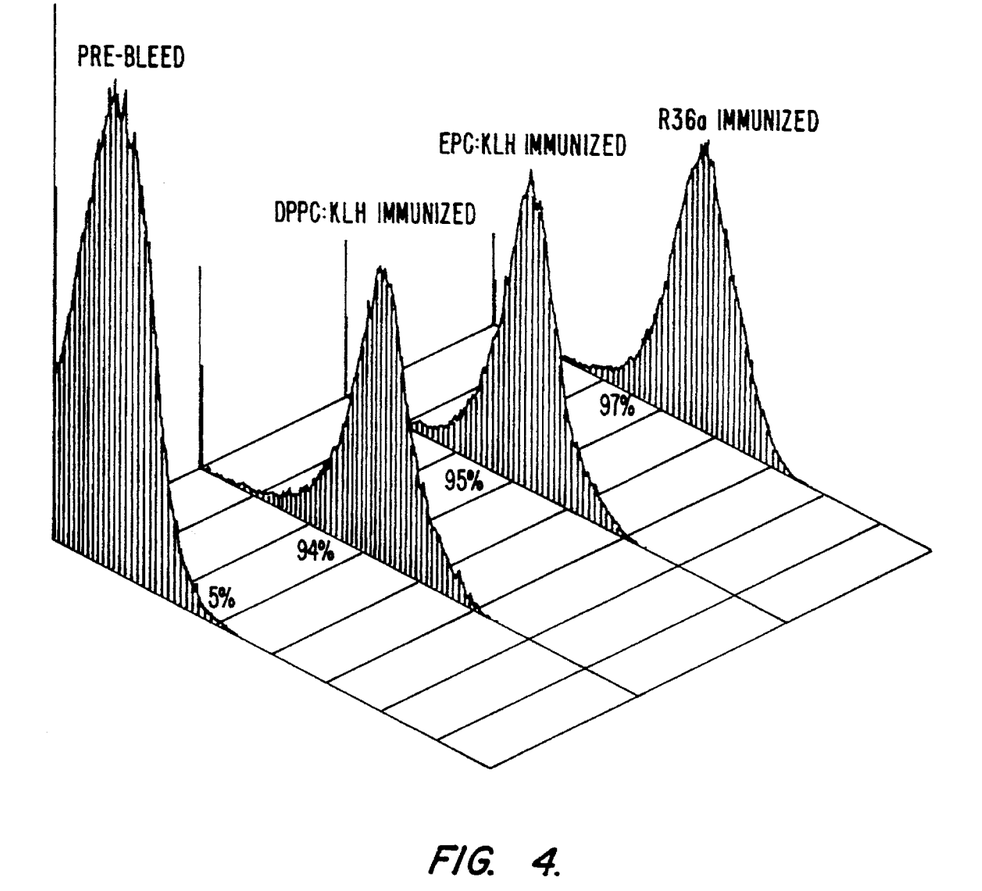
FIG. 4. FCM analysis of serum samples from BALB/C mice immunized with R36a, DPPC:KLH and EPC:KLH.
Figure 5:
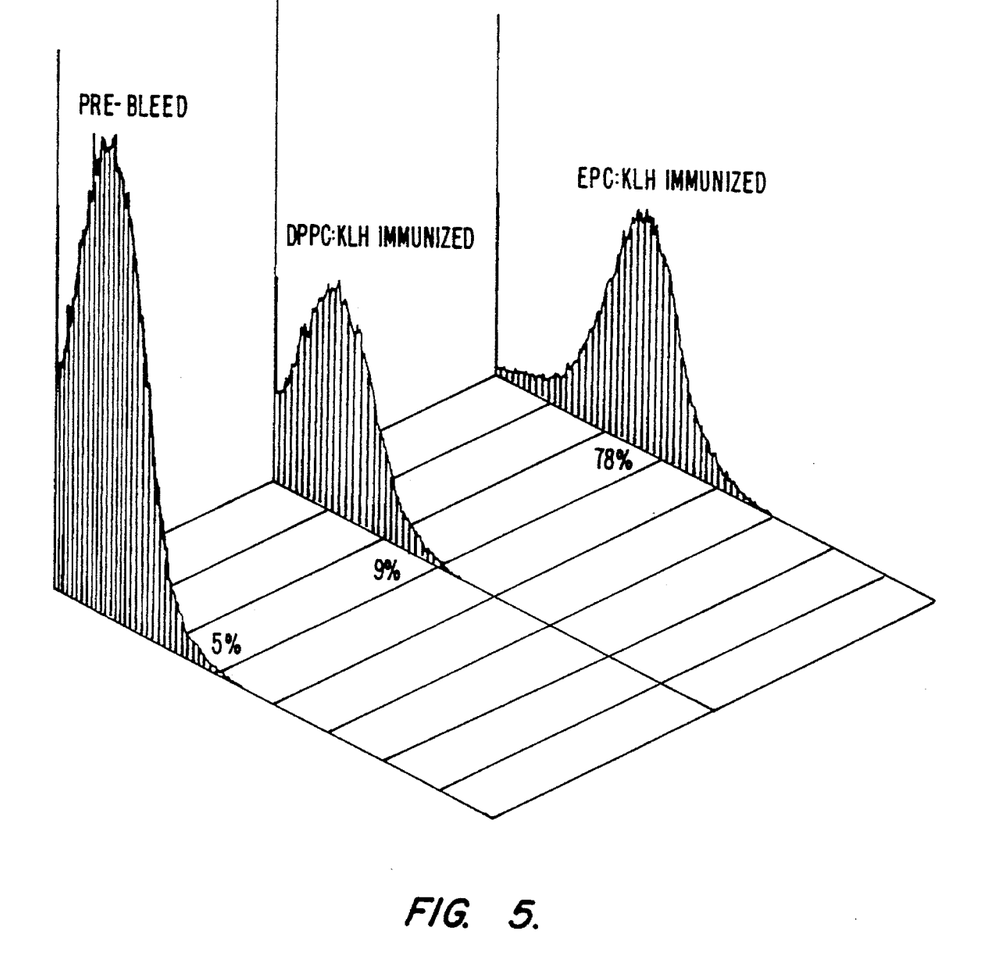
FIG. 5. FCM analysis of serum samples from C.CBA/N xid mice immunized with R36a, DPPC:KLH and EPC:KLH.

Antiserum from normal animals immunized with any of the antigens, all of which provided protection against challenge with the WU-2, were capable of binding to the WU-2. See FIG. 4. In contrast, only the antiserum from the EPC:KLH immunized xid mice was capable of binding to the WU-2, while the antiserum from the DPPC:KLH and R36a immunized xid mice failed to bind to the bacteria. See FIG. 5. Thus, the ability of EPC:KLH generated antibodies to protect naive xid animals from challenge with the virulent WU-2 strain is positively correlated with the ability of the antibodies to bind to the bacteria as predicted. This confirms that the immunoprotection to *S. pneumoniae* challenge observed in xid mice following immunization with EPC-KLH is in fact due to the PC-specific antibodies generated in these mice.

It is understood that the examples and embodiments described herein are for illustrative purposes only and that various modifications or changes in light thereof will be suggested to persons skilled in the art and are to be included within the spirit and preview of this application and scope of the appended claims.

What is claimed is:

1. A composition capable of eliciting an immune response to phosphocholine in a mammal comprising a phosphocholine conjugate of the formula:

wherein:

X is selected from the group consisting of O, S, NH, or CH$_2$;

Y is a straight chain alkyl group; and

R is an immunological carrier.

2. The composition of claim 1 wherein X is O.

3. The composition of claim 1 wherein Y is (CH$_2$)$_5$.

4. The composition of claim 1 wherein R is keyhole limpet hemocyanin.

5. The composition of claim 1 wherein X is O, Y is (CH$_2$)$_5$ and R is keyhole limpet hemocyanin.

6. A vaccine for inducing immunoprotection in a mammal against phosphocholine antigen-containing pathogenic organisms, said vaccine consisting of pharmaceutically acceptable excipients and a phosphocholine conjugate of the formula:

wherein:

X is selected from the group consisting of O, S, NH, or $CH_2$;

Y is a straight chain alkyl group; and

R is an immunological carrier; said composition being present in an amount effective to induce immunoprotection against said organisms.

7. The vaccine of claim 6 wherein said pathogenic organism is a bacterium.

8. The vaccine of claim 7 wherein said bacterium is *Streptococcus pneumoniae*.

9. A method of protecting a mammal from infection by a phosphocholine antigen-containing pathogenic organism, said method comprising the administration of a vaccine consisting of pharmaceutically acceptable excipients and an amount of the PC conjugate of the formula:

wherein:

X is selected from the group consisting of O, S, NH, or $CH_2$;

Y is a straight chain alkyl group; and

R is a soluble polymer;

and wherein said amount is effective for inducing immunoprotection against infection by said organism.

10. A method of claim 9 wherein said pathogenic organism is a bacterium.

11. A method of claim 10 wherein said bacterium is *S. pneumoniae*.

12. The composition of claim 6 wherein X is O.

13. The composition of claim 6 wherein Y is $(CH_2)_5$.

14. The composition of claim 6 wherein R is keyhole limpet hemocyanin.

15. The composition of claim 7 wherein X is O, Y is $(CH_2)_5$, and R is keyhole limpet hemocyanin.

16. The composition of claim 4 wherein X is O.

17. The composition of claim 9 wherein Y is $(CH_2)_5$.

18. The composition of claim 9 wherein R is keyhole limpet hemocyanin.

19. The composition of claim 9 wherein X is O, Y is $(CH_2)_5$, and R is keyhole limpet hemocyanin.

* * * * *

UNITED STATES PATENT AND TRADEMARK OFFICE
CERTIFICATE OF CORRECTION

PATENT NO. : 5,455,032
APPLICATION NO. : 08/099205
DATED : October 3, 1995
INVENTOR(S) : James J. Kenny and Dan L. Longo

It is certified that error appears in the above-identified patent and that said Letters Patent is hereby corrected as shown below:

On the title page, item [75], should read:

[75] Inventors: James J. Kinney, Rockville; Dan L. Longo, Kensington, both of Md.

Signed and Sealed this

Sixth Day of March, 2007

JON W. DUDAS
*Director of the United States Patent and Trademark Office*